(12) United States Patent
Haraguchi et al.

(10) Patent No.: US 8,648,056 B2
(45) Date of Patent: Feb. 11, 2014

(54) COMPOSITION FOR LOCAL ANESTHESIA

(75) Inventors: Mitsuhiro Haraguchi, Kawasaki (JP); Yoshihiko Kawasaki, Yokohama (JP)

(73) Assignee: Showa Yakuhin Kako Co., Ltd., Tokyo (JP)

( * ) Notice: Subject to any disclaimer, the term of this patent is extended or adjusted under 35 U.S.C. 154(b) by 579 days.

(21) Appl. No.: 11/408,921

(22) Filed: Apr. 24, 2006

(65) Prior Publication Data

US 2006/0189572 A1  Aug. 24, 2006

Related U.S. Application Data

(62) Division of application No. 10/451,377, filed as application No. PCT/JP02/00082 on Jan. 10, 2002, now abandoned.

(30) Foreign Application Priority Data

Jan. 10, 2001  (JP) ................................ 2001-002120
Jul. 6, 2001  (JP) ................................ 2001-206259

(51) Int. Cl.
*A01N 43/04* (2006.01)
*A01N 37/44* (2006.01)

(52) U.S. Cl.
USPC ........................................... 514/54; 514/537

(58) Field of Classification Search
None
See application file for complete search history.

(56) References Cited

U.S. PATENT DOCUMENTS

| | | | |
|---|---|---|---|
| 4,105,706 A | | 8/1978 | Szejtili et al. |
| 4,105,760 A | * | 8/1978 | Szejtli et al. ............ 514/54 |
| 5,446,070 A | * | 8/1995 | Mantelle ............ 514/772.6 |
| 5,585,398 A | | 12/1996 | Ernst |
| 5,624,962 A | * | 4/1997 | Takeuchi et al. ........ 514/772.2 |
| 5,747,060 A | * | 5/1998 | Sackler et al. ............ 424/426 |
| 5,814,621 A | * | 9/1998 | Kanaya et al. ............ 514/54 |
| 5,827,529 A | | 10/1998 | Ono et al. |
| 5,914,118 A | * | 6/1999 | Yamamura et al. ........ 424/402 |
| 6,007,843 A | | 12/1999 | Drizen et al. |
| 6,074,674 A | | 6/2000 | Jay et al. |
| 6,083,933 A | | 7/2000 | Hahn |
| 6,123,957 A | * | 9/2000 | Jernberg ............ 424/435 |
| 6,325,993 B1 | | 12/2001 | Saito et al. |
| 6,391,336 B1 | * | 5/2002 | Royer ............ 424/468 |
| 6,455,030 B2 | | 9/2002 | Saito et al. |
| 6,921,541 B2 | * | 7/2005 | Chasin et al. ............ 424/426 |

FOREIGN PATENT DOCUMENTS

| | | |
|---|---|---|
| CA | 1070681 | 1/1980 |
| EP | 0507160 | 10/1992 |
| GB | 1570627 | 7/1980 |
| JP | 2000-256189 | 9/2000 |
| WO | 97/07794 | 3/1997 |
| WO | 99/04764 | 2/1999 |
| WO | 99/15150 | 4/1999 |
| WO | 00/50004 | 8/2000 |

OTHER PUBLICATIONS

Paavola et al., "Controlled Release of Lidocaine from Injectable Gels and Efficacy in Rat Sciatic Nerve Block", Pharmaceutical Research, vol. 12, No. 12, 1995, pp. 1997-2002.
"Xylocaine Cartridge for Dental Use", Fujisawa Pharmaceutical Co., Ltd.
Collins, Principles of Anesthesiology, Second Edition, Chapter 45 "Local Anesthetics", Lea and Febiger, Philadelphia, 1976, pp. 865-887.
Dental Outlook, Special Edition, "Medical Practice of Tooth Extraction", 4. Dental Local Anesthetics, 1979, pp. 84-94.
"Pharmacology", co-edited by Takagi and Ozawa, published by Nanzan-doh Co., Ltd., 1976, pp. 202-205.
Journal of Japanese Dental Society of Anesthesiology, 16, 1988, pp. 10-22.
Journal of Japanese Dental Society of Anesthesiology, 27, 1999, pp. 158-164.
Paavola et al., "Controlled Release of Lidocaine from Injectable Gels and Efficacy in Rat Sciatic Nerve Block", Pharmaceutical Research, vol. 12, No. 12, pp. 1997-2002 (1995).
U.S. Appl. No. 10/538,061, published as U.S. Patent Application Publication No. 2006/0216245 A1 (Haraguchi et al.) on Sep. 28, 2006 and entitled, "Composition for Local Anesthesia".
Heske A.H., "Xylocaine: 50 years of clinical service to dentistry," Texas Dental Journal, (1998), 115, No. 5, pp. 9-13.
Japanese Office action mailed Apr. 12, 2011 25, 2011 in JP 2001-206259 with English translation.
Ishida et al., Chem. Pharm. Bull., vol. 30, No. 3, 1982, pp. 980-984.
Japanese Office action mailed Jan. 25, 2011 with English translation.

\* cited by examiner

*Primary Examiner* — Kyle Purdy
(74) *Attorney, Agent, or Firm* — Greenblum & Bernstein, P.L.C.

(57) ABSTRACT

A composition for local anesthesia which comprises a local anesthetic as an active ingredient and an agent for maintaining anesthetic action selected from the group consisting of acidic mucopolysaccharides such as sodium chondroitin sulfate and cellulose derivatives such as hydroxypropylmethylcellulose, and does not contain catecholamines, which has durability of anesthetic action suitable for minor dental operations such as tooth extraction, and can be used as a safe composition for local anesthesia used for oral surgery or dental treatment.

4 Claims, No Drawings

COMPOSITION FOR LOCAL ANESTHESIA

CROSS-REFERENCE TO RELATED APPLICATIONS

This application is a divisional of application Ser. No. 10/451,377, filed Jan. 10, 2002, which is a National Stage Application of International Application No. PCT/JP02/00082, filed Jan. 10, 2002, which was not published in English under PCT Article 21(2), entering the National Stage on Jul. 2, 2003, and which claims priority of Japanese Application Nos. 2001-002120, filed Jan. 10, 2001; and 2001-206259, filed Jul. 6, 2001. The entire disclosure of application Ser. No. 10/451,377 is considered as being part of this application, and the entire disclosure of application Ser. No. 10/451,377 is expressly incorporated by reference herein in its entirety.

TECHNICAL FIELD

The present invention relates to a composition for local anesthesia. More specifically, the present invention relates to a safe composition for local anesthesia which has durability of action suitable for minor dental operations such as tooth extraction.

BACKGROUND ART

For operations in the fields of oral surgery and dental treatment, in particular, for tooth extraction and the like in the field of dental treatment, anesthetics for local injection (agents for local anesthesia) containing lidocaine (2-diethylamino-N-(2,6-dimethyl-phenyl)acetamide) as an active ingredient have been used. For example, "Xylocaine Cartridge for Dental Use" (Fujisawa Pharmaceutical Co., Ltd.) has been clinically used. This agent for local anesthesia is a composition for topical administration which contains 20 mg of lidocaine hydrochloride and 0.0125 mg of epinephrine per 1 ml of a solution for injection. The agent is generally used in an amount of 0.3-1.8 ml to carry out infiltration anesthesia or block anesthesia (see, a package insert of the drug).

Agents for local anesthesia are generally formulated with a catecholamine such as epinephrine which has angiotonic effect on local capillary blood vessels to reduce blood flow. The effect of the catecholamine is to decrease bleeding in a field of operation by lowering blood flow, and to reduce transmigration (diffusion) of an anesthetic agent being an active ingredient into blood and maintain high concentration of the anesthetic agent in the local tissue to achieve a prolonged local anesthetic effect (Collins, V. J., Principles of Anesthesiology, 2nd Ed., Lea and Febiger, Philadelphia, 1976; as a review about agents for dental local anesthesia, see, Dental Outlook, special edition, "Medical practice of tooth extraction," 4. Dental local anesthetics, pp. 84-94, 1979).

However, because epinephrine contained in topically administered anesthetics may possibly cause vasoconstriction in other tissues or in the whole body, it has been so far pointed out that local anesthetics containing epinephrine have possibilities of danger for administration to patients with hypertonia, anteriosclerosis, cardiac failure, hyperthyreosis, or diabetes or a patient who has experienced angiospasm. Therefore, the administration of the drug is a contraindication in principle (The term "contraindication in principle" means that an administration to the above patients is not allowed in principle, and when an administration is particularly required the administration needs to be performed very carefully: Announcement in June, 2000, by Chief of safety measure Division of Pharmaceutical and Medical Safety Bureau of Ministry of Health and Welfare).

In dental lidocaine preparations which are clinically used, epinephrine is mixed at 1/80,000 (g/ml, 0.0125 mg per ml). For the purpose of decreasing side effects of epinephrine, anesthetics for dental use containing about 1/200,000 (g/ml) of epinephrine (0.005 mg as a free base per ml) are proposed as compositions for local anesthesia having durability suitable for short-time dental operations such as tooth extraction (WO 97/07794). By using said anesthetics, necessary and sufficient durability of anesthetic action for minor dental operations and the like can be achieved, however, the possibility of side effects of epinephrine can not be completely eliminated. Therefore, other means for maintaining the action of local anesthetics are desired to be provided.

DISCLOSURE OF THE INVENTION

An object of the present invention is to provide a composition for local anesthesia which has excellent durability of action. More specifically, the object of the present invention is to provide a safe composition for local anesthesia which has durability of action suitable for minor dental operations such as tooth extraction and oral surgery operations without using catecholamines.

The inventors of the present invention conducted intensive researches to achieve the foregoing objects, and as a result, they found that a material selected from the group consisting of acidic mucopolysaccharides such as sodium chondroitin sulfate and cellulose derivatives such as hydroxypropylmethylcellulose has a function to significantly maintain anesthetic action of local anesthetics such as lidocaine hydrochloride. The present invention was achieved on the basis of these findings.

The present invention thus provides a composition for local anesthesia which comprises a local anesthetic as an active ingredient and an agent for maintaining anesthetic action selected from the group consisting of acidic mucopolysaccharides and cellulose derivatives, and does not contain catecholamines. The aforementioned composition for local anesthesia is preferably provided as a composition for local anesthesia used for oral surgery or dental treatment. According to the preferred embodiment of the present invention, there are provided the aforementioned composition for local anesthesia wherein the local anesthetic is lidocaine hydrochloride; the aforementioned composition for local anesthesia wherein the acidic mucopolysaccharide is sodium chondroitin sulfate; and the aforementioned composition for local anesthesia wherein the cellulose derivative is hydroxypropylmethylcellulose.

From another aspect, the present invention provides an agent for maintaining anesthetic action of a local anesthetic selected from the group consisting of acidic mucopolysaccharides and cellulose derivatives. According to the preferred embodiment of the present invention, there are provided the aforementioned agent for maintaining action wherein the local anesthetic is lidocaine hydrochloride; the aforementioned agent for maintaining action wherein the acidic mucopolysaccharide is sodium chondroitin sulfate; the aforementioned agent for maintaining action wherein the cellulose derivative is hydroxypropylmethylcellulose.

From further aspect, the present invention provides a use of a substance selected from the group consisting of acidic mucopolysaccharides and cellulose derivatives for manufacture of the aforementioned local anesthetics; a method for maintaining anesthetic action of a local anesthetic comprising the step of topically administering a substance selected from the group consisting of acidic mucopolysaccharides and cellulose derivatives together with a local anesthetic.

BEST MODE FOR CARRYING OUT THE INVENTION

Types of the local anesthetics which are contained in the composition of the present invention are not particularly limited. Examples include cocaine analogues such as cocaine and tropacocaine; water-soluble esters of aminobenzoic acid such as procaine and tetracaine; esters of benzoic acid such as piperocaine and stovaine; esters of alkoxybenzoic acid such as cyclomethycaine and parethoxycaine; aminoketones such as diclonine and falicain; aminoethers such as pramoxine; benzofuranone derivatives such as amolanone; amidine or guanidine derivatives such as phenacaine; urethane derivatives such as diperodon; quinoline or isoquinoline derivatives such as dibucaine; amino acid anilides such as lidocaine; alkylesters of aminobenzoic acid such as ethyl aminobenzoate.

The classification of the aforementioned local anesthetics is described for convenience according to the classification described in Table 32 at pages from 202 to 205 in "Pharmacology" co-edited by Takagi and Ozawa, published by Nanzan-doh Co., Ltd. as the second issue in 1976. However, it should be understood that classifications other than the above are acceptable and the active ingredient of the composition of the present invention is not limited to the above examples. These local anesthetics are generally used in forms of physiologically acceptable salts. Examples of such salts include mineral acid salts such as hydrochloride and sulfate. Among them, a local anesthetic selected from the group consisting of lidocaine, procaine, tetracaine, dibucaine, and salts thereof may preferably be used. More preferably, a local anesthetic selected from the group consisting of lidocaine hydrochloride, procaine hydrochloride, tetracaine hydrochloride, and dibucaine hydrochloride may be used. Lidocaine hydrochloride may most preferably be used.

The acidic mucopolysaccharide used as an agent for maintaining anesthetic action of a local anesthetic in the composition of the present invention is a heteropolysaccharide which is widely present in connective tissues in animals, and two saccharides consisting of repetition unit are hexosamine and glucuronic acid. Types of the acidic mucopolysaccharide are not particularly limited, and the examples include chondroitin sulfate and hyaluronic acid. Salts of the acidic mucopolysaccharide can also be used. An example of the acidic mucopolysaccharide preferred for the composition of the present invention includes chondroitin sulfate. Sodium chondroitin sulfate is most preferable. Sodium chondroitin sulfate is commercially available as an extract from gristles of mammals or fishes, and easily obtainable.

As the cellulose derivatives used as an agent for maintaining anesthetic action of a local anesthetic in the composition of the present invention, ether derivatives of cellulose may be used. Examples of ether derivatives of cellulose include hydroxypropylcellulose and hydroxypropylmethylcellulose. Esterified cellulose ether derivatives such as hydroxypropylmethylcellulose phthalate may also be used. An example of cellulose derivative preferable for the composition of the present invention includes hydroxypropylmethylcellulose. Products of various standard depending on ratios of introduction of methoxy group and hydroxypropoxy group are available as hydroxypropylmethylcellulose. Among them, hydroxypropylmethylcellulose 2208, 2906 and 2910 listed in Japanese Pharmacopoeia are preferred, all of which are easily available as commercial products (for example, Metolose produced by Shin-Etsu Chemical Co., Ltd.).

One or more types of the agent for maintaining anesthetic action selected from the group consisting of acidic mucopolysaccharides and cellulose derivatives can be mixed in the composition of the present invention. A combined use of acidic mucopolysaccharide and cellulose derivatives is also a preferred embodiment. A content of the agent for maintaining anesthetic action selected from the group consisting of acidic mucopolysaccharides and cellulose derivatives can be suitably selected depending on the type of the agent for maintaining anesthetic action, the type of the local anesthetic, and desired duration and anesthetic depth, and generally selected approximately in a range of 0.1 g to 10 g based on 1 g of local anesthetic. Anesthetic duration of the composition for local anesthesia is easily and precisely determined by the methods described in, for example, Journal of Japanese Dental Society of Anesthesiology, 16, pp. 10-22, 1988; and Journal of Japanese Dental Society of Anesthesiology, 27, pp. 158-164, 1999. The methods are specifically described in Examples of specification.

The composition for local anesthesia of the present invention can be provided as a composition for injection in a form of an aqueous solution in which the aforementioned components and optional pharmaceutical additives, which are available for those skilled in the art as additives to be formulated in compositions for topical injections, are dissolved in distilled water for injection. The composition for local anesthesia of the present invention can also be prepared as a pharmaceutical preparation in a dried form such as a lyophilized preparation, and dissolved when used. Generally, the composition is provided for clinical use after being filled in ampoules, vials, cartridges or the like under sterile condition. As the pharmaceutical additives, for example, isotonicities to adjust osmotic pressure ratio to about 0.8-1.3, preferably about 1.0, e.g., sodium chloride; pH modifiers to adjust pH to a range of about 3.0-7.5, preferably 3.3-7.0, e.g., hydrochloric acid or sodium hydroxide; antiseptics, e.g., methyl p-hydroxybenzoate, and the like may be used.

The composition for local anesthesia of the present invention can be suitably used for minor operations in oral surgery and dental treatment, preferably for operations which can be completed in several to ten minutes such as tooth extraction in dental treatment. However, applicable operations are not limited to the uses in the oral surgery and dental treatment, and the composition can be used for surgical local anesthesia such as for skin incision. The agent for maintaining action of a local anesthetic contained in the composition of the present invention prolongs duration of the action of a local anesthetic, and has an effect of increasing anesthetic depth as well. Therefore, the composition for local anesthesia of the present invention has increased intensity and durability of local anesthesia without using catecholamines such as epinephrine, and has a feature that the composition can be used as a safe local anesthetic even to patients with hypertonia, anteriosclerosis, cardiac failure, hyperthyreosis, or diabetes or a patient who has experienced angiospasm.

The composition of the present invention can be prepared by a method well-known to those skilled in the art. Specific examples of the method for producing the composition of the present invention are detailed in the following examples. However, methods for preparing the composition of the present invention are not limited to those described in the examples, and appropriate alterations and modifications can be added to these methods.

EXAMPLES

The present invention will be explained more specifically by referring to the following examples. However, the scope of the present invention is not limited to these examples.

Example 1

Comparative Example

Citric acid (1 g) and lidocaine hydrochloride (2 g) were dissolved in distilled water for injection (80 ml). After being adjusted to pH 4 by addition of a sufficient quantity of hydrochloric acid, the solution was added with distilled water for injection up to the total volume of 100 ml to prepare a composition for local anesthesia.

Example 2

Comparative Example

Glycerol (1 g) and lidocaine hydrochloride (2 g) were dissolved in distilled water for injection (80 ml). After being adjusted to pH 4 by addition of a sufficient quantity of hydrochloric acid, the solution was added with distilled water for injection up to the total volume of 100 ml to prepare a composition for local anesthesia.

Example 3

Comparative Example

Benzethonium chloride (0.1 g) and lidocaine hydrochloride (2 g) were dissolved in distilled water for injection (80 ml). After being adjusted to pH 4 by addition of a sufficient quantity of hydrochloric acid, the solution was added with distilled water for injection up to the total volume of 100 ml to prepare a composition for local anesthesia.

Example 4

The Present Invention: Lidocaine pH 4 Group

Sodium chondroitin sulfate (1 g) and lidocaine hydrochloride (2 g) were dissolved in distilled water for injection (80 ml). After being adjusted to pH 4 by addition of a sufficient quantity of hydrochloric acid, the solution was added with distilled water for injection up to the total volume of 100 ml to prepare the composition for local anesthesia of the present invention.

Example 5

The Present Invention

Hydroxypropylmethylcellulose (1 g) and lidocaine hydrochloride (2 g) were dissolved in distilled water for injection (80 ml). After being adjusted to pH 4 by addition of a sufficient quantity of hydrochloric acid, the solution was added with distilled water for injection up to the total volume of 100 ml to prepare the composition for local anesthesia of the present invention.

Example 6

The Present Invention

Sodium chondroitin sulfate (1 g), hydroxypropylmethylcellulose (1 g) and lidocaine hydrochloride (2 g) were dissolved in distilled water for injection (80 ml). After being adjusted to pH 4 by addition of a sufficient quantity of hydrochloric acid, the solution was added with distilled water for injection up to the total volume of 100 ml to prepare the composition for local anesthesia of the present invention.

Example 7

The Present Invention: Lidocaine pH 6 Group

Sodium chondroitin sulfate (1 g) and lidocaine hydrochloride (2 g) were dissolved in distilled water for injection (80 ml). After being adjusted to pH 6 by addition of a sufficient quantity of sodium hydroxide, the solution was added with distilled water for injection up to the total volume of 100 ml to prepare the composition for local anesthesia of the present invention.

Example 8

The Present Invention: Lidocaine pH 7 Group

Sodium chondroitin sulfate (1 g) and lidocaine hydrochloride (2 g) were dissolved in distilled water for injection (80 ml). After being adjusted to pH 7 by addition of a sufficient quantity of sodium hydroxide, the solution was added with distilled water for injection up to the total volume of 100 ml to prepare the composition for local anesthesia of the present invention.

Test Example

Wistar male rats of 7 to 8-week old having weights from 190 g to 260 g were used. Thiamylal sodium was intraperitoneally administered, and tracheotomy and endotracheal intubation were conducted, and the experiment was conducted under light anesthesia and spontaneous respiration. A stimulating electrode was inserted into the upper incisor pulp of the rat, and electrically simulated. Somatosensory evoked potential (SEP) of the rat was recorded from the contralateral surface of the skull, and the SEP amplitudes [P1-N1] were measured. Fifty μl of each combination were injected into the palate paraperiosteally. Measurements were carried out 22 times: an average of three times before the injection of the test solution was used as a control value; just after the injection; at every 2 minutes until 10 minutes after the injection; and then at every 5 minutes up to 30 minutes; and thereafter at every 10 minutes up to 120 minutes and each value was calculated in percentage relative to the control value. When the effect of local anesthesia was disappeared and recovery was observed, the measurements were terminated at that point. The [P1-N1] value obtained in each point was converted in a percentage value relative to the value before the infiltration anesthesia as a control. The results are shown in the following Table 1. For examples 4, 7, and 8, average values are shown for a group of n=6.

In the table, the unit is shown in percentage and the values near 100 percent indicate disappearance of anesthetic intensities. Reference 1 is a composition for local anesthesia prepared in such a manner that lidocaine hydrochloride (2 g) was dissolved in distilled water for injection (80 ml), and after being adjusted to pH 4 by adding a sufficient quantity of hydrochloric acid, the solution was added with distilled water for injection up to the total volume of 100 ml. The control 2 is a commercial local anesthetic which comprises lidocaine hydrochloride (2 g), epinephrine hydrogen tartrate (2.5 mg), and sodium pyrosulfite (60 mg) (pH 4) (ORA® Inj. Cartridge, produced by Showa Yakuhin Kako Co., Ltd.). It is clearly understood that the same level of duration and intensity of anesthesia were obtained by using the composition for local anesthesia of the present invention (Example 4 to 6) as that of the commercial composition for local anesthesia comprising epinephrine (reference 2).

TABLE 1

| Time (minute) | Example | | | | | | | | Reference | |
|---|---|---|---|---|---|---|---|---|---|---|
| | 1 | 2 | 3 | 4 | 5 | 6 | 7 | 8 | 1 | 2 |
| Control | 100 | 100 | 100 | 100 | 100 | 100 | 100 | 100 | 100 | 100 |
| 0 | 61.9 | 62.0 | 93.2 | 62.8 | 54.7 | 51.7 | 67.2 | 71.2 | 65.5 | 28.5 |
| 2 | 37.7 | 45.1 | 46.9 | 33.1 | 15.5 | 8.9 | 45.6 | 36.2 | 56.4 | 26.1 |
| 4 | 45.8 | 31.7 | 40.7 | 19.6 | 13.8 | 8.0 | 26.9 | 23.4 | 48.9 | 16.5 |
| 6 | 34.8 | 20.2 | 24.1 | 15.7 | 9.7 | 3.7 | 24.8 | 15.0 | 42.3 | 10.9 |
| 8 | 31.1 | 14.7 | 39.8 | 17.0 | 8.4 | 0.5 | 20.8 | 14.0 | 45.4 | 6.9 |
| 10 | 28.1 | 14.6 | 52.7 | 15.2 | 5.4 | 3.1 | 21.2 | 11.4 | 34.4 | 6.9 |
| 15 | 52.7 | 50.5 | 58.2 | 16.0 | 6.3 | 3.6 | 20.2 | 13.7 | 30.0 | 2.4 |
| 20 | 69.4 | 81.3 | 73.1 | 18.6 | 15.0 | 4.8 | 16.2 | 11.6 | 39.4 | 8.2 |
| 25 | 73.7 | 126.8 | 97.5 | 26.2 | 21.0 | 10.0 | 20.4 | 12.9 | 52.8 | 10.2 |
| 30 | 86.6 | | 94.1 | 31.0 | 19.6 | 16.3 | 19.5 | 12.6 | 58.6 | 14.4 |
| 40 | 97.2 | | 110.2 | 51.8 | 25.6 | 16.9 | 32.7 | 19.2 | 84.0 | 18.8 |
| 50 | 104.9 | | | 68.5 | 25.1 | 28.3 | 46.8 | 26.9 | 83.0 | 30.6 |
| 60 | | | | 87.4 | 43.5 | 28.6 | 60.7 | 33.1 | 108.3 | 46.2 |
| 70 | | | | 98.6 | 55.3 | 50.8 | 69.8 | 51.6 | | 57.4 |
| 80 | | | | 107.4 | 72.4 | 73.2 | 79.2 | 70.7 | | 57.4 |
| 90 | | | | 116.0 | 83.8 | 92.8 | 89.9 | 85.9 | | 70.8 |
| 100 | | | | 110.3 | 80.3 | 92.9 | 93.1 | 92.2 | | 93.3 |
| 110 | | | | 115.2 | 83.1 | 99.5 | 98.3 | 98.2 | | 103.3 |
| 120 | | | | 110.5 | 95.9 | 93.2 | 100.9 | 110.1 | | 102.2 |

INDUSTRIAL APPLICABILITY

The composition for local anesthesia of the present invention has increased intensity and durability of local anesthesia without using catecholamines such as epinephrine, and is useful as a safe composition for local anesthesia used for short-time dental operations such as tooth extraction and oral surgery operations.

What is claimed is:

1. A method of maintaining local anesthesia during oral surgery or dental treatment comprising administering to a mammal a composition for local anesthesia during oral surgery or dental treatment which comprises an aqueous solution of dissolved local anesthetic and dissolved acidic mucopolysaccharide, which solution does not contain a catecholamine.

2. The method according to claim 1, wherein the local anesthesia is lidocaine.

3. The method according to claim 1, wherein the acidic mucopolysaccharide is sodium chondroitin sulfate.

4. The method according to claim 2, wherein the acidic mucopolysaccharide is sodium chondroitin sulfate.

* * * * *